United States Patent
Lemaner

(10) Patent No.: US 8,511,515 B2
(45) Date of Patent: Aug. 20, 2013

(54) FLUID PRODUCT DISPENSING DEVICE

(75) Inventor: Francois Lemaner, La Vallee Montaure (FR)

(73) Assignee: Aptar France SAS, Le Neubourg (FR)

( * ) Notice: Subject to any disclaimer, the term of this patent is extended or adjusted under 35 U.S.C. 154(b) by 289 days.

(21) Appl. No.: 12/993,001

(22) PCT Filed: Jun. 16, 2009

(86) PCT No.: PCT/FR2009/051137
§ 371 (c)(1), (2), (4) Date: Nov. 16, 2010

(87) PCT Pub. No.: WO2009/153513
PCT Pub. Date: Dec. 23, 2009

(65) Prior Publication Data
US 2011/0062188 A1   Mar. 17, 2011

(30) Foreign Application Priority Data
Jun. 17, 2008 (FR) ...................................... 08 53995

(51) Int. Cl.
*B67D 7/84* (2010.01)

(52) U.S. Cl.
USPC .... 222/162; 222/321.8; 222/381; 222/402.15

(58) Field of Classification Search
USPC .................. 222/1, 162, 321.8, 381, 160, 163, 222/175, 183, 325, 402.15
See application file for complete search history.

(56) References Cited

U.S. PATENT DOCUMENTS

| 3,164,301 | A | * | 1/1965 | Hargreaves et al. | 239/676 |
| 3,559,574 | A | * | 2/1971 | Gates | 101/366 |
| 3,963,145 | A | * | 6/1976 | Fegley et al. | 222/5 |
| 3,967,757 | A | * | 7/1976 | Fegley | 222/5 |
| 4,167,245 | A | * | 9/1979 | Kock et al. | 239/11 |
| 4,771,769 | A | * | 9/1988 | Hegemann et al. | 128/200.22 |
| 5,487,489 | A | | 1/1996 | Weiss et al. | |
| 5,667,142 | A | * | 9/1997 | Newman | 239/346 |
| 6,527,144 | B2 | * | 3/2003 | Ritsche et al. | 222/162 |

(Continued)

FOREIGN PATENT DOCUMENTS

| EP | 1 183 194 B1 | 3/2004 |
| EP | 1 974 827 A1 | 10/2008 |

(Continued)

OTHER PUBLICATIONS

EPO Office Action for 09 766 075.7-2425, dated Oct. 31, 2012, Partial Machine Translation.

*Primary Examiner* — Kevin P Shaver
*Assistant Examiner* — Christopher Bahr
(74) *Attorney, Agent, or Firm* — Sughrue Mion, PLLC

(57) ABSTRACT

A fluid dispenser device including a body, a reservoir, a dispenser head, and a dispenser member. The dispenser member includes a dispenser-member body and a movable member that moves axially in the dispenser-member body during actuation. The device includes a lateral actuator system secured to the body and having an actuator element that co-operates with the reservoir, with the dispenser member, or with an element secured to the reservoir and/or the dispenser member. The actuator element is movable between a rest position and an actuated position. The body includes a guide surface for guiding the actuator element, the guide surface is stationary relative to the dispenser head, and substantially parallel to the movement axis of the movable member in the dispenser-member body during actuation.

21 Claims, 4 Drawing Sheets

(56) References Cited

U.S. PATENT DOCUMENTS

| | | | |
|---|---|---|---|
| 6,860,411 B2 * | 3/2005 | Stradella | 222/321.8 |
| 8,062,264 B2 * | 11/2011 | Godfrey et al. | 604/181 |
| 2002/0134798 A1 | 9/2002 | Lamboux | |
| 2003/0197025 A1 * | 10/2003 | Cabarroque et al. | 222/162 |
| 2004/0254450 A1 * | 12/2004 | Griffin et al. | 600/411 |
| 2007/0131717 A1 | 6/2007 | Davies et al. | |
| 2007/0138207 A1 * | 6/2007 | Bonney et al. | 222/162 |
| 2007/0164049 A1 * | 7/2007 | Bonney et al. | 222/162 |
| 2008/0237264 A1 | 10/2008 | Auerbach et al. | |

FOREIGN PATENT DOCUMENTS

| | | |
|---|---|---|
| FR | 2 812 826 A1 | 2/2002 |
| FR | 2 859 464 A1 | 3/2005 |
| WO | 01/03851 A1 | 1/2001 |
| WO | 2005/075105 A1 | 8/2005 |
| WO | 2006/005962 A1 | 1/2006 |
| WO | 2009/068877 A1 | 6/2009 |

* cited by examiner

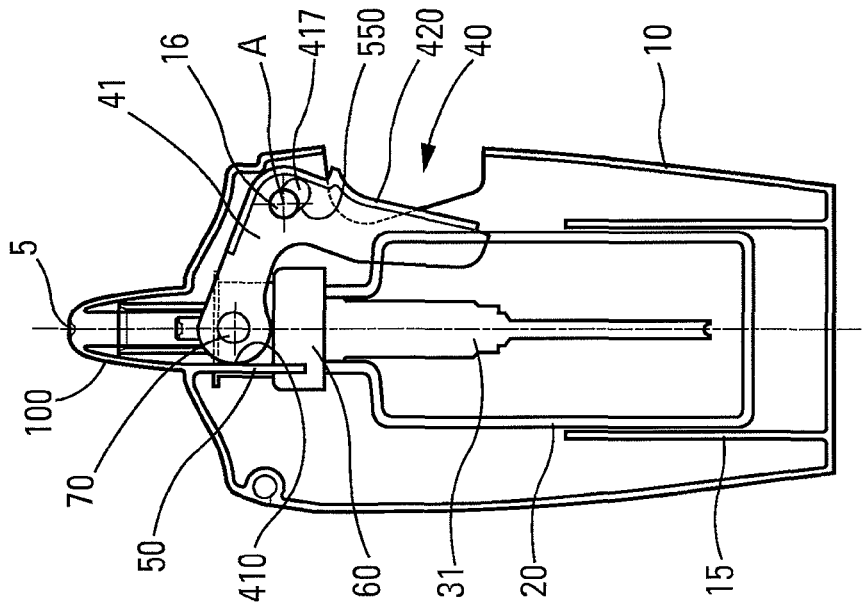
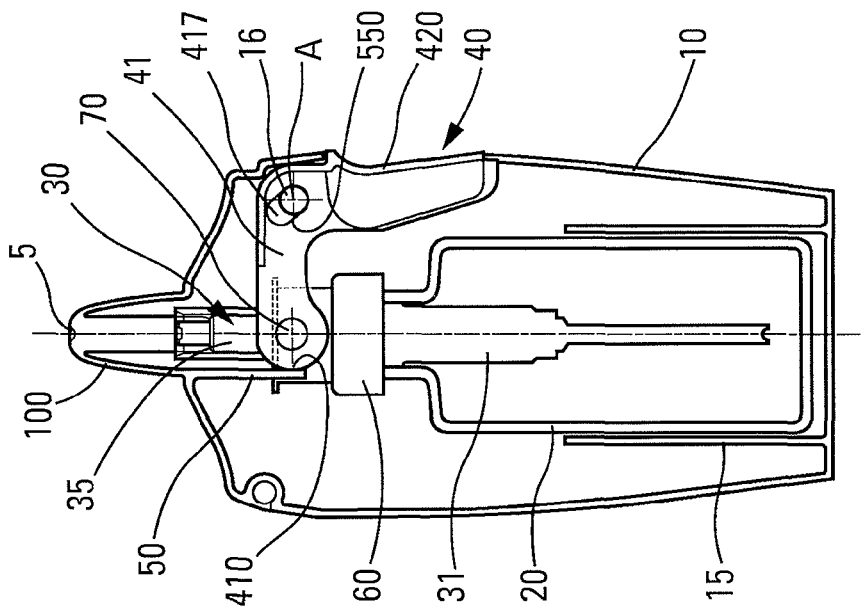

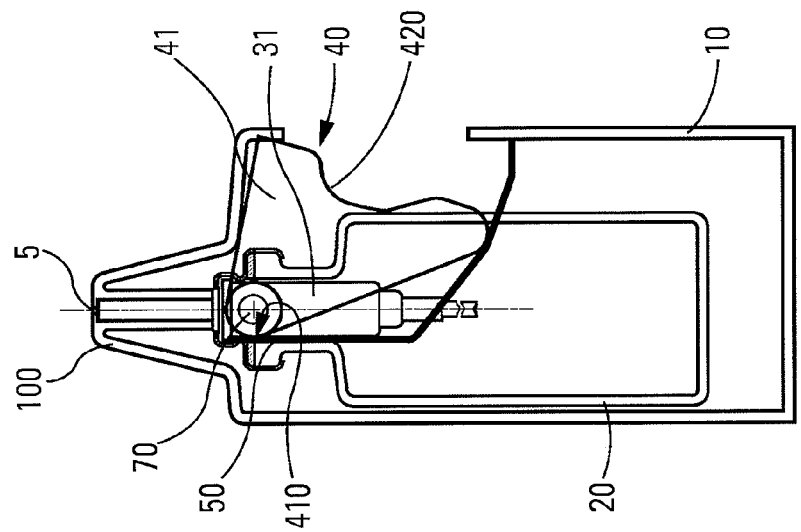
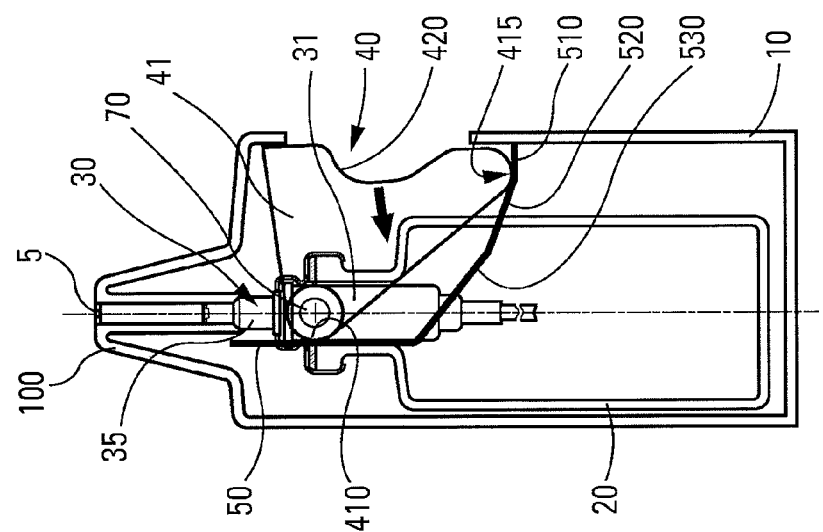

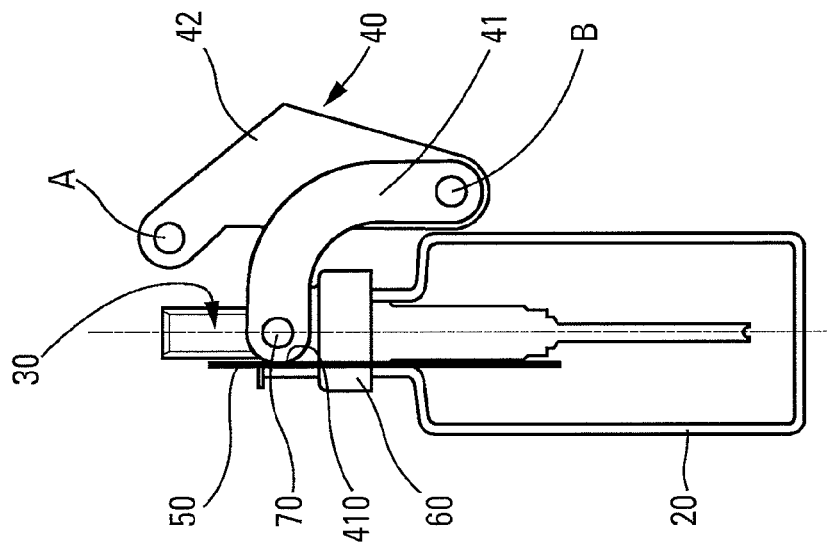
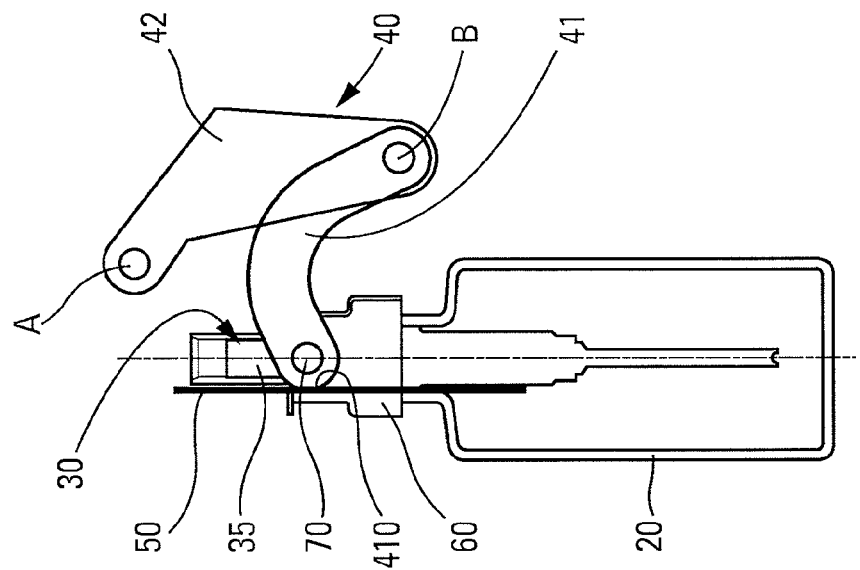

FLUID PRODUCT DISPENSING DEVICE

The present invention relates to a fluid dispenser device, and more particularly to a nasal-spray device for a pharmaceutical.

Fluid dispenser devices are well known in the state of the art. They generally include a reservoir containing the fluid, on which reservoir there is assembled a dispenser member, e.g. a pump or a valve, that is generally actuated by means of a dispenser head for selectively dispensing the fluid contained inside said reservoir. The dispenser head includes a dispenser orifice through which the fluid is sprayed, e.g. into the user's nose for a nasal-spray device. Numerous devices of this type are actuated manually by the user by moving the reservoir and the dispenser head axially against each other, thereby actuating the dispenser member. However, this type of device presents drawbacks, in particular when the device is of the nasal-spray type, since the axial force exerted by the user in order to actuate the device leads to a risk of the dispenser head moving inside the user's nostril, with risks of injury and/or of the fluid not being dispensed completely or properly on actuation. In order to remedy this problem, lateral actuator devices have been proposed, generally including a lever that is pivotally mounted on a body and that has an inner portion that is adapted to co-operate with one of the dispenser head and the reservoir so as to move said element against the other, and thus actuate the dispenser member. However, such devices induce radial stresses during actuation, which stresses may also have negative influences on the spraying of the composition into the user's nostril. Document WO 2005/075105 describes a prior-art device.

An object of the present invention is to provide a fluid dispenser device that does not have the above-mentioned drawbacks.

Another object of the present invention is to provide a fluid dispenser device, in particular a nasal spray, that guarantees safe and reliable actuation of the device on each actuation, without risk of injury to the user.

More particularly, an object of the present invention is to provide a fluid dispenser device that is simple and inexpensive to manufacture and to assemble.

The present invention thus provides a fluid dispenser device comprising: a body; a reservoir; a dispenser head incorporating a dispenser orifice; and a dispenser member, such as a pump or a valve, that is mounted on said reservoir, said dispenser member comprising a dispenser-member body and a movable member that moves axially in said dispenser-member body while said dispenser member is being actuated; said device further comprises a lateral actuator system that is secured to said body, said lateral actuator system comprising at least one actuator element that co-operates with said reservoir, with said dispenser member, or with an element that is secured to said reservoir and/or to said dispenser member, said at least one actuator element being movable between a rest position in which said dispenser member is not actuated, and an actuated position in which said dispenser member is actuated, said body including at least one guide surface for guiding said at least one actuator element, said guide surface being stationary relative to said dispenser head, and substantially parallel to the movement axis of the movable member in the dispenser-member body while said dispenser member is being actuated.

Advantageously, said at least one actuator element includes a rounded contact zone that co-operates with said guide surface over the entire actuation stroke.

Advantageously, said guide surface is secured to the dispenser head incorporating the dispenser orifice.

Advantageously, said at least one actuator element co-operates with a respective projection that is secured to the reservoir, to the dispenser member, or to an element that is secured to the reservoir and/or to the dispenser member.

Advantageously, said at least one projection (70) is secured to a ring (60) that is assembled on said reservoir (20).

Advantageously, said ring fastens the dispenser member on the reservoir.

Advantageously, said at least one actuator element includes an eyelet that is mounted around said projection, said actuator element pivoting about said projection during actuation.

Advantageously, said lateral actuator system includes a presser element that is mounted on the body to pivot about an axis (A), said at least one actuator element being mounted on said presser element to pivot about an axis (B).

Advantageously, said presser element includes a presser zone against which the user presses during actuation.

Advantageously, said axis (A) is further from the dispenser orifice than said axis (B).

Advantageously, said axis (A) is closer to the dispenser orifice than said axis (B).

Advantageously, said actuator element includes a presser zone against which the user presses during actuation.

Advantageously, the body includes a second guide surface that slopes relative to the guide surface.

Advantageously, said second guide surface comprises at least two, preferably three, portions of different slopes, which portions co-operate with a second rounded contact zone of said actuator element.

Advantageously, said second guide surface comprises a first portion that co-operates with the actuator element in its rest position, a second portion that co-operates with the actuator element during its actuation stroke, and a third portion that co-operates with the actuator element in its actuated position.

Advantageously, said second guide surface is connected to the guide surface.

Advantageously, said second guide surface is formed by an oblong opening that is formed in said actuator element, said oblong opening receiving a pin that is secured to the body and that defines the pivot axis (A) of the actuator element.

Advantageously, said oblong opening has a width that is approximately equal to the width of said pin, and a length that is greater than the length of said pin.

Advantageously, said body includes an axial guide sleeve for guiding the reservoir during actuation.

These characteristics and advantages and others of the present invention appear more clearly from the following detailed description of several embodiments thereof, given by way of non-limiting example, and with reference to the accompanying drawings, and in which:

FIGS. 3 and 4 are diagrammatic views of a second embodiment of the present invention, respectively in the rest position and in the actuated position;

FIGS. 5 and 6 are diagrammatic views of a third embodiment of the present invention, respectively in the rest position and in the actuated position; and FIGS. 7 and 8 are diagrammatic views of a fourth embodiment of the present invention, respectively in the rest position and in the actuated position;

Figure 1:
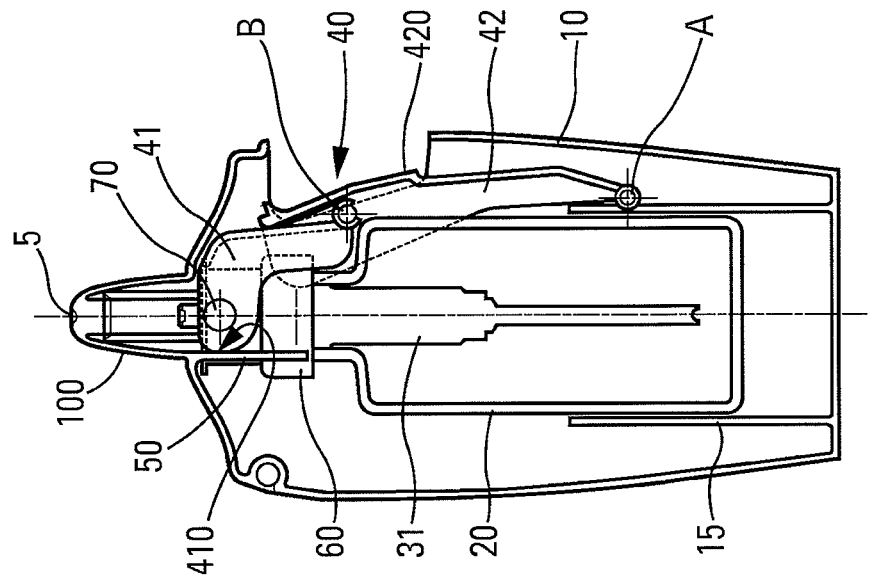
FIGS. 1 and 2 are diagrammatic views of a first embodiment of the present invention, respectively in the rest position and in the actuated position.
Figure 2:
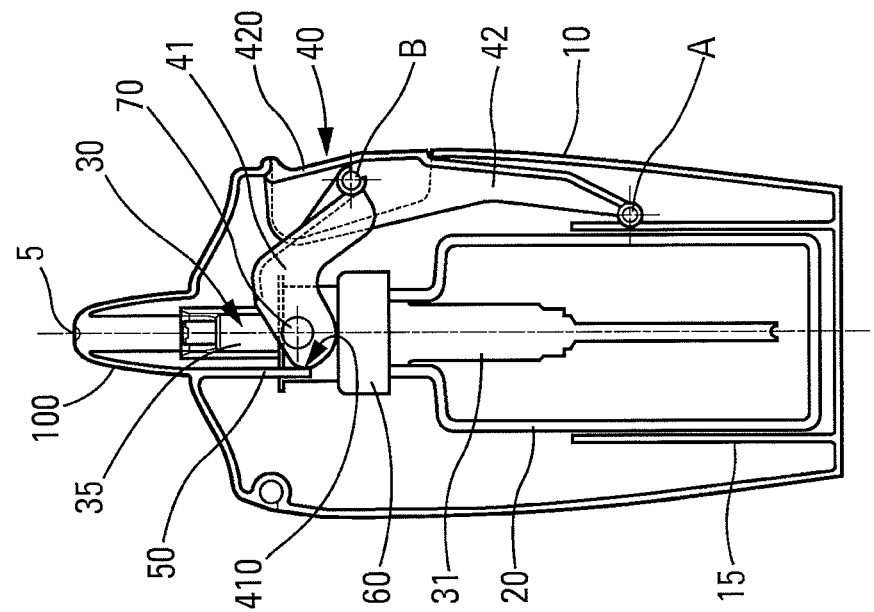

With reference to FIGS. 1 and 2, which show a first advantageous embodiment of the invention, the fluid dispenser device includes a body 10 in which there is assembled a reservoir 20 that contains fluid, in particular a pharmaceutical, for spaying into the user's nose. A dispenser member 30, such as a pump or a valve, is assembled on said reservoir 20, advantageously by means of a fastener ring 60. The dispenser member comprises a dispenser-member body 31, such as a pump body or a valve body, and a movable member 35, such as a piston rod or a valve member, that is slidably mounted in said dispenser-member body. In conventional manner, the movable member 35 is driven into the dispenser-member body 31, so as to actuate said dispenser member 30. This is shown very diagrammatically in the drawings, with the movable member 35 in its high position in FIGS. 1, 3, 5, and 7 (rest position), and in its driven-in position in FIGS. 2, 4, 6, and 8 (actuated position). Advantageously, a dispenser head 100 is assembled on said dispenser member 30, said dispenser head 100 incorporating a dispenser orifice 5 through which the fluid is dispensed. In the embodiments shown, the head 100 forms part of, or is secured to, the body 10 of the device. It may be made integrally with said body.

The device includes a lateral actuator system 40 that is secured to the body 10 and that is adapted to co-operate with the reservoir 20, with the dispenser member 30, or with an element that is secured to said reservoir 20 and/or to said dispenser member 30, e.g. the fastener ring 60 that fastens the dispenser member 30 to the reservoir 20. Optionally, a separate ring could be fastened to the reservoir or to the fastener ring 60 for co-operating with the lateral actuator system. The lateral actuator system 40 includes an actuator element 41. In the embodiment in FIGS. 1 and 2, the actuator element 41 is mounted on a presser element 42 to pivot about an axis B. The presser element 42 itself is mounted on the body 10 to pivot about an axis A. The embodiment in FIGS. 1 and 2 thus includes two interconnected pivot elements, the user pressing on the presser element 42, preferably via a presser zone 420 so as to cause the presser element 42 to pivot relative to the body 10, about the axis A, the pivoting of the presser element 42 causing the actuator element 41 to pivot relative to said presser element 42, about the axis B, and thus causing the dispenser member 30 to be actuated. The actuator element 41 advantageously co-operates with a projection 70 that may be secured either to the reservoir 20 or to the dispenser member 30, or to an element that is secured to the reservoir and/or to the dispenser member. Advantageously, the projection 70 is formed on a ring 60 that is assembled on said reservoir, and the ring 60 advantageously serves to fasten the dispenser member 30 on the reservoir.

In the invention, the body 10 of the device includes at least one guide surface 50 that serves to guide the actuator element 41 during its actuation stroke, i.e. while it is pivoting when the user actuates the lateral actuator system 40. As shown in FIGS. 1 and 2 in particular, the guide surface 50 is vertical and axial, i.e. it is substantially parallel to the movement axis of the movable member 35 in the dispenser-member body 31 while the dispenser member 30 is being actuated. The guide surface 50 is preferably plane. It is stationary relative to the dispenser head during actuation. The guide surface thus serves to reduce, and in particular to eliminate, the radial stresses that are exerted by the lateral actuator system 40 while the device is being actuated. In this way, when the user actuates the device, there is no longer any risk of the dispenser head 100 moving sideways in the nostril, with the risk of all or some of the composition being ejected inappropriately. Advantageously, the actuator element 41 includes a rounded contact zone 410 for co-operating with the guide surface 50 over the entire actuation stroke. This enables friction against the guide surface to be minimized, so as to minimize the impact of the presence of the guide surface 50 on the resistance of the lateral actuator system to being actuated. In the embodiment in FIGS. 1 and 2, the guide surface 50 is secured to the dispenser head 100, but naturally the guide surface 50 could be disposed in another location of the device that is more appropriate. As shown in the figures, the body advantageously includes an axial guide sleeve 15 that receives and guides the reservoir 20 while it is moving inside the body while the device is being actuated. Preferably, the guide sleeve 15 is disposed in the bottom portion of the body when the device is in its upright position, as shown in the figures.

FIGS. 3 and 4 show a second embodiment that differs from the embodiment in FIGS. 1 and 2 mainly in that it uses a lateral actuator system 40 that comprises only one pivot element, namely the actuator element 41. In this variant, it is thus the actuator element 41 that includes the presser zone 420 against which the user presses so as to actuate the device. The axial guide surface 50 and the way the actuator element 41 co-operates with the unit formed of the reservoir and of the dispenser member in order to perform the actuation are similar to those described with reference to FIGS. 1 and 2. However, in this second embodiment, the actuator element 41 needs to be able to move a little relative to its pivot axis A, so as to guarantee that, over its entire actuation stroke, it remains in permanent contact with the axial guide surface 50. Advantageously, this may be achieved by forming an oblong opening 417 in the actuator element 41, said oblong opening 417 coming to be assembled around a pin 16 that is secured to the body 10, said pin defining the pivot axis A. Advantageously, and as shown in FIGS. 3 and 4, the oblong opening slopes when the device is viewed in its upright position shown in the figures, and the width of the oblong opening is approximately equal to (while being very slightly greater than) the width of said pin 16, whereas its length is greater than the length of the pin, thereby making it possible for the actuator element 41 to slide along the sloping oblong opening while it is pivoting about the axis A. The inside of the oblong opening 417 thus forms a second guide surface 550 that slopes relative to the guide surface 50. The shape of the second guide surface 550 and its angle of inclination, depend on the shape of the rounded contact zone 410 of the actuator element 41 that co-operates with the guide surface 50. The purpose is to guarantee permanent thrust, so as to limit, or even eliminate, the radial stresses that are exerted on the body of the device during actuation.

FIGS. 5 and 6 show a third embodiment of the present invention. In this third embodiment, the pivoting lateral actuator system 40 comprises a single actuator element 41 that incorporates the presser zone 420 against which the user presses so as to actuate the device in the direction of the arrow shown in FIG. 5. In this embodiment, the guide surface 50 is not secured directly to the dispenser head, but is connected to another portion of the body 10 by means of a second guide surface that is formed of three portions 510, 520, 530 in this embodiment. Thus, in this variant, the pivot axis of the actuator element 41 is formed by the pin 70 that is secured to the reservoir 20 and/or to the dispenser member 30 and/or to an element that is secured to the reservoir and/or to the dispenser member. The actuator element 41 thus co-operates both with the axial guide surface 50 (i.e. that is vertical in the upright position shown in the figures) via its rounded contact zone 410, and also with the second guide surface by means of a second contact zone 415. Preferably, the contact zone 415 is also rounded. With reference more precisely to the embodiment in FIGS. 5 and 6, the second guide surface includes a first portion 510, which is substantially horizontal in the upright position shown in FIG. 5, that co-operates with the actuator element 41 when the device is in its rest position. The first portion 510 is extended by a second portion 520 that forms an angle relative to the first portion 510, and with which the actuator element 41 co-operates during the actuation stroke of the device. Finally, a third portion 530 connects the second portion 520 to the axial guide surface 50, and the actuator element 41 comes to co-operate with the third portion 530 when the device is in its actuated position. Naturally, this particular shape of second guide surface made in three portions that slope relative to one another is not essential, and a second guide surface formed by a single portion that slopes relative to the guide surface 50 could be envisaged, the purpose being, once again, to guarantee that the radial stresses that are exerted by the lateral actuator system during actuation are reduced or even eliminated.

FIGS. 7 and 8 show a fourth embodiment of the present invention. In this embodiment, the lateral actuator system 40 once again includes two elements that are mounted to pivot relative to each other, in a manner similar to the first embodiment described with reference to FIGS. 1 and 2. It should be observed that in FIGS. 7 and 8, the device is shown only in part. Thus, the lateral actuator system 40 includes an actuator element 41 that on one side co-operates by means of the projection 70 with the reservoir 20, with the dispenser member 30, or with an element that is secured to the reservoir and/or to the dispenser member, such as the fastener ring 60. The actuator element 41 also co-operates with the guide surface 50 of the invention. Then, the actuator element 41 is pivotally mounted on an intermediate presser element 42 that is shown diagrammatically in FIGS. 7 and 8, and that is itself mounted on the body to pivot about a pivot axis A. When the user presses on the presser element 42, said presser element pivots about the axis A, thereby causing the actuator element 41 to pivot about its axis B, and the device to be actuated. In principle, this actuation is similar to the actuation in FIGS. 1 and 2, but in this embodiment the axis A is closer to the dispenser orifice 5 than is the axis B, whereas in the first embodiment in FIGS. 1 and 2, the axis A is further from the dispenser orifice 5 than is the axis B. In the embodiment in FIGS. 7 and 8, the actuator element 41 thus comes to co-operate with the projection 70 from below, so as to actuate the device.

In the various embodiments described above, the actuator element 41 pivots about the projection 70 with which it co-operates. When the actuator element 41 co-operates with such a projection 70, it preferably includes an eyelet that is mounted around said projection 70, thereby enabling said actuator element to pivot about said projection. Naturally, in a variant, it could be envisaged that the actuator element 41 co-operates in some other way with a portion of the reservoir, of the dispenser member, or of an element that is secured to the reservoir and/or to the dispenser member, e.g. by pushing from below against any appropriate profile, or by means of a cam surface that makes it possible for the dispenser member 30 to be moved axially while the lateral actuator system 40 is being actuated laterally.

It should be observed that the axial guide wall of the invention could also be used with an actuator system that is axial and not lateral, e.g. a conventional nasal-spray actuator that can be actuated axially by the user. Used in this way, the guide wall makes it possible to guide said actuator during its actuation stroke, avoiding any risk of "tilting" or offsetting, in the event of the user applying a force that is not completely axial. The presence of the guide wall thus prevents any risk of poor actuation likely to block the pump, cause leaks, or dispense an incomplete dose.

Other modifications could be envisaged by the person skilled in the art, without going beyond the ambit of the present invention, as defined by the accompanying claims.

The invention claimed is:

1. A fluid dispenser device comprising: a body; a reservoir; a dispenser head incorporating a dispenser orifice; and a dispenser member that is mounted on said reservoir, said dispenser member comprising a dispenser-member body and a movable member that moves axially in said dispenser-member body while said dispenser member is actuated; said device further comprises a lateral actuator system that is secured to said body, said lateral actuator system comprising at least one actuator element that co-operates with said reservoir, with said dispenser member, or with an element secured to at least one of said reservoir and to said dispenser member, said at least one actuator element movable between a rest position in which said dispenser member is not actuated, and an actuated position in which said dispenser member is actuated; said body includes at least one guide surface for guiding said at least one actuator element, said guide surface being stationary relative to said dispenser head, and substantially parallel to the axial movement of the movable member in the dispenser-member body while said dispenser member is being actuated; and wherein said lateral actuator system includes a presser element that is mounted on the body to pivot about a first axis, said at least one actuator element mounted on said presser element to pivot about a second axis.

2. The device according to claim 1, wherein said at least one actuator element includes a rounded contact zone that co-operates with said guide surface over an entire actuation stroke.

3. The device according to claim 1, wherein said guide surface is secured to the dispenser head incorporating the dispenser orifice.

4. The device according to claim 1, wherein said at least one actuator element co-operates with a respective projection that is secured to the reservoir, or to the dispenser member, or to an element that is secured to the reservoir or to the dispenser member.

5. The device according to claim 4, wherein said at least one projection is secured to a ring that is assembled on said reservoir.

6. The device according to claim 5, wherein said ring fastens the dispenser member on the reservoir.

7. The device according to claim 4, wherein said at least one actuator element includes an eyelet that is mounted around said projection, said actuator element pivoting about said projection during actuation.

8. The device according to claim 1, wherein said presser element includes a presser zone against which the user presses during actuation.

9. The device according to claim 1, wherein said first axis is further from the dispenser orifice than said second axis.

10. The device according to claim 1, wherein said first axis is closer to the dispenser orifice than said second axis.

11. The device according to claim 1, wherein said actuator element includes a presser zone against which the user presses during actuation.

12. The device according to claim 1, wherein the body includes a second guide surface that slopes relative to the guide surface.

13. The device according to claim 12, wherein said second guide surface comprises at least two portions of different slopes, which portions co-operate with another rounded contact zone of said actuator element.

14. The device according to claim 13, wherein said second guide surface comprises a first portion that co-operates with the actuator element in its rest position, a second portion that co-operates with the actuator element during an actuation stroke of the actuator element, and a third portion that co-operates with the actuator element in the actuated position of the actuator element.

15. The device according to claim 14, wherein said second guide surface is connected to the guide surface.

16. The device according to claim 12, wherein said second guide surface is formed by an oblong opening that is formed in said actuator element, said oblong opening receiving a pin that is secured to the body and that defines a pivot axis of the actuator element.

17. The device according to claim 16, wherein said oblong opening has a width that is approximately equal to a width of said pin, and a length that is greater than a length of said pin.

18. The device according to claim 1, wherein said body includes an axial guide sleeve for guiding the reservoir during actuation.

19. The device according to claim 1, wherein dispenser member is a pump or a valve.

20. The device according to claim 12, wherein said second guide surface comprises at least three portions of different slopes, which portions co-operate with another rounded contact zone of said actuator element.

21. The device according to claim 16, wherein the pivot axis of the actuator element is the first pivot axis.

* * * * *